(12) United States Patent  
Matsunami et al.

(10) Patent No.: US 9,936,911 B2
(45) Date of Patent: Apr. 10, 2018

(54) BODY FLUID COLLECTION DEVICE AND TESTING DEVICE

(71) Applicant: Sosaikouseikai Clinical Foundation Matsunami Research Park, Gifu (JP)

(72) Inventors: Hidetoshi Matsunami, Gifu (JP); Kuniaki Saito, Aichi (JP); Yushi Matuo, Osaka (JP); Masao Takemura, Gifu (JP)

(73) Assignee: SOSAIKOUSEIKAI CLINICAL FOUNDATION MATSUNAMI RESEARCH PARK, Gifu (JP)

( * ) Notice: Subject to any disclaimer, the term of this patent is extended or adjusted under 35 U.S.C. 154(b) by 0 days.

(21) Appl. No.: 15/021,429

(22) PCT Filed: Sep. 5, 2014

(86) PCT No.: PCT/JP2014/073477
§ 371 (c)(1),
(2) Date: Mar. 11, 2016

(87) PCT Pub. No.: WO2015/037530
PCT Pub. Date: Mar. 19, 2015

(65) Prior Publication Data
US 2016/0213295 A1 Jul. 28, 2016

(30) Foreign Application Priority Data
Sep. 12, 2013 (JP) .................. 2013-189094

(51) Int. Cl.
*A61B 5/00* (2006.01)
*B65D 81/00* (2006.01)
(Continued)

(52) U.S. Cl.
CPC ........ *A61B 5/150732* (2013.01); *A61B 5/157* (2013.01); *A61B 5/150022* (2013.01);
(Continued)

(58) Field of Classification Search
CPC ........ A61B 5/150022; A61B 5/150389; A61B 5/150572; A61B 5/150732;
(Continued)

(56) References Cited

U.S. PATENT DOCUMENTS 5,054,499 A * 10/1991 Swierczek ........... A61B 5/1411
600/480
5,636,640 A * 6/1997 Staehlin ............... A61B 5/1411
600/577
(Continued)

FOREIGN PATENT DOCUMENTS

CN 1466436 A 1/2004
DE 102 58 016 A1 6/2004
(Continued)

OTHER PUBLICATIONS

International Search Report issued in Application No. PCT/JP2014/073477 dated Oct. 7, 2014.
(Continued)

*Primary Examiner* — Devin Henson
(74) *Attorney, Agent, or Firm* — Pearne & Gordon LLP (57) ABSTRACT

A testing device according to the present invention includes a housing including a skin surface sheet and an upper surface cover. A hollow needle configured to interlock with the upper surface cover and a testing reagent or equipment are accommodated in the housing. Through deformation of the upper surface cover by application of an external force, the hollow needle perforates the skin. A body fluid flows in the space inside of the housing and is brought into contact with the testing reagent or equipment to acquire information on the body fluid. Through recovery of the upper surface cover to an original shape by elimination of the external force, the hollow needle again becomes accommodated in the housing.

9 Claims, 4 Drawing Sheets (51) Int. Cl.
  *A61B 5/15* (2006.01)
  *A61B 5/151* (2006.01)
  *A61B 5/157* (2006.01)
(52) U.S. Cl.
  CPC .... *A61B 5/150099* (2013.01); *A61B 5/15105* (2013.01); *A61B 5/15142* (2013.01); *A61B 5/150389* (2013.01); *A61B 5/150969* (2013.01); *A61B 5/150977* (2013.01); *A61B 5/150572* (2013.01); *A61B 5/150748* (2013.01)
(58) Field of Classification Search
  CPC ........ A61B 5/150748; A61B 5/150969; A61B 5/150977; A61B 5/15105; A61B 5/15142; A61B 5/157
  See application file for complete search history.

(56) References Cited

U.S. PATENT DOCUMENTS

| | | | |
|---|---|---|---|
| 7,207,952 | B2 | 4/2007 | Takinami |
| 2003/0109808 | A1 | 6/2003 | Takinami |
| 2005/0015019 | A1* | 1/2005 | Honda ................. A61B 5/1411 600/576 |
| 2005/0245844 | A1* | 11/2005 | Mace ................... A61B 5/1411 600/583 |
| 2008/0275327 | A1 | 11/2008 | Faarbaek |
| 2012/0275955 | A1 | 11/2012 | Haghgooie |
| 2012/0277629 | A1 | 11/2012 | Bernstein |
| 2013/0172704 | A1* | 7/2013 | Kuenstner ........... A61B 5/1411 600/347 |

FOREIGN PATENT DOCUMENTS

| | | |
|---|---|---|
| DE | 20 2008 010 918 U1 | 12/2008 |
| JP | H08-182761 A | 7/1996 |
| JP | 2006-284481 A | 10/2006 |
| JP | 2008-532596 A | 8/2008 |
| JP | 2011-069800 A | 4/2011 |
| WO | 2012/149134 A1 | 11/2012 |

OTHER PUBLICATIONS

Office Action in Chinese Patent Application No. 201480050554.0 dated Sep. 2, 2016.
Extended European Search Report issued in Patent Application No. EP 14 84 3377 dated Sep. 12, 2016.

* cited by examiner

BODY FLUID COLLECTION DEVICE AND TESTING DEVICE

TECHNICAL FIELD

The present invention relates to a body fluid collection device and a testing device.

BACKGROUND ART

Collection of a body fluid, such as blood, to acquire information on the body fluid has been carried out. For example, in diagnosis of an infectious disease, a healthcare professional, such as a doctor, collects a body fluid from a test subject using a body fluid collecting instrument, such as a blood collection needle and a syringe barrel, and then takes the body fluid out of the body fluid collecting instrument at another place to test the body fluid. In this case, there are risks of misidentification of body fluid samples collected and body fluid samples tested. Further, there may be infection risks of healthcare professionals through an operation for collecting a body fluid and testing the body fluid, and infection risks owing to the body fluid collecting instrument and testing instrument after disposal.

For this reason, there is a disclosure of immunochromatography using an antibody capable of recognizing an antigen derived from a virus to judge the presence or absence of an infectious virus at a place of a blood collection operation (Patent Literature 1). When the collected blood is taken out of a container for collected blood and subjected to the immunochromatography, the presence or absence of infection can be judged visually, and thus the risks of misidentification of body fluid samples can be reduced. However, even in this case, the infection risks owing to wastes are not eliminated. Further, the method requires an operation for taking out collected blood and an operation for testing the blood, and hence there is still a problem of infection risks of healthcare professionals. In addition, in this technology, the blood collection operation needs to be performed at a place in which test equipment has been set.

Further, there is a disclosure of a method involving attaching an extendable cover surrounding a needle for blood collection (Patent Literature 2). In this case, exposure of the needle can be prevented before and after the operation for collecting blood and after disposal, but the method requires an operation for testing components in blood. Accordingly, there is still a possibility of infection of healthcare professionals due to a needle after blood collection and blood droplets. Therefore, the problem of infection risks of the healthcare professionals has not been eliminated.

CITATION LIST

Patent Literature

[PTL 1] JP 2011-69800 A
[PTL 2] JP 08-182761 A

SUMMARY OF INVENTION

Technical Problem

An object of the present invention is to provide a body fluid collection device capable of eliminating infection risks of healthcare professionals and infection risks owing to wastes and can collect a body fluid through a short-time and simple operation.

Another object of the present invention is to provide a testing device capable of eliminating infection risks of healthcare professionals and infection risks owing to wastes, can collect a body fluid through a short-time and simple operation regardless of place and situation to acquire information on the body fluid, and can prevent misidentification of body fluid samples.

According to an embodiment of the present invention, there is provided a body fluid collection device. The device includes a housing including a skin surface sheet capable of adhering tightly to a skin and an upper surface cover having elasticity; and a hollow needle configured to interlock with the upper surface cover and accommodated in the housing. At least part of a space in the housing communicates with an interior of the hollow needle, and the body fluid collection device is configured such that: through deformation of the upper surface cover by application of an external force in a direction of the skin surface sheet to the upper surface cover with the skin surface sheet adhering tightly to the skin, the hollow needle penetrates the skin surface sheet to perforate the skin, and a body fluid flows in the space communicating with the interior of the hollow needle through the hollow needle; and through recovery of the upper surface cover to an original shape by elimination of the external force, the hollow needle again becomes accommodated in the housing.

According to another embodiment of the present invention, there is provided a testing device for collecting a body fluid and acquiring information on the body fluid collected. The device includes a housing including a skin surface sheet capable of adhering tightly to a skin and an upper surface cover having elasticity; a hollow needle configured to interlock with the upper surface cover and accommodated in the housing; and testing means accommodated in the housing. At least part of a space in the housing communicates with an interior of the hollow needle, and the testing device is configured such that: through deformation of the upper surface cover by application of an external force in a direction of the skin surface sheet to the upper surface cover with the skin surface sheet adhering tightly to the skin, the hollow needle penetrates the skin surface sheet to perforate the skin, and a body fluid flows in the space communicating with the interior of the hollow needle through the hollow needle and is brought into contact with the testing means to acquire information on the body fluid; and through recovery of the upper surface cover to an original shape by elimination of the external force, the hollow needle again becomes accommodated in the housing.

In one embodiment of the present invention, the testing device further includes an inner support configured to support the hollow needle and arranged in the upper surface cover on an inside of the housing.

In one embodiment of the present invention, the inner support has a sheet shape and is supported by the upper surface cover so that the inner support is approximately parallel to the skin surface sheet.

In one embodiment of the present invention, the hollow needle supported by the inner support penetrates the inner support, and the inner support divides the space in the housing into a space communicating with the interior of the hollow needle and a space not communicating with the interior of the hollow needle.

In one embodiment of the present invention, the inner support is brought into contact with the skin surface sheet when the hollow needle perforates the skin.

In one embodiment of the present invention, the inner support includes a lower spacer configured to project in an opposite direction to the skin surface sheet.

In one embodiment of the present invention, the upper surface cover includes, on an inner surface of the housing, an upper spacer configured to project in a direction of the skin surface sheet.

In one embodiment of the present invention, the space communicating with the interior of the hollow needle is maintained in a reduced pressure state until the hollow needle perforates the skin.

In one embodiment of the present invention, the testing device further includes, as another member, a lower surface cover attachable to a surface of the skin surface sheet, the lower surface cover having a thickness equal to or longer than a length of the hollow needle.

In one embodiment of the present invention, the testing device further includes body fluid pretreatment means arranged in the hollow needle and/or the space communicating with the interior of the hollow needle, wherein the body fluid having flowed therein is subjected to pretreatment by the body fluid pretreatment means.

Advantageous Effects of Invention

According to the body fluid collection device of the present invention, the body fluid flows in the space communicating with the interior of the hollow needle in the housing, and the hollow needle after collection is accommodated in the housing. Thus, infection risks of healthcare professionals and infection risks owing to wastes can be eliminated. Further, the body fluid can be collected through a short-time and simple operation.

According to the testing device of the present invention, the body fluid flows in the space communicating with the interior of the hollow needle in the housing, and the hollow needle after collection is accommodated in the housing. Thus, infection risks of healthcare professionals and infection risks owing to wastes can be eliminated. In addition, the testing means is accommodated in the housing, and hence the body fluid can be collected through a short-time and simple operation regardless of place and situation to acquire information on the body fluid. Further, misidentification of body fluid samples can be prevented because it is not necessary to move the body fluid from a place where the body fluid is collected to acquire information on the body fluid and it is also not necessary to supply the body fluid to equipment for acquiring information on the body fluid.

DESCRIPTION OF EMBODIMENTS

A. Testing Device
A-1. Outline of Testing Device

Embodiments of the present invention are described below with reference to the drawings, but the present invention is not limited to these embodiments. It should be noted that, for convenience sake, a testing device is described first, and a body fluid collection device is described later. It should be noted that the term "body fluid" as used herein refers to any appropriate liquid derived from a test subject. The body fluid may contain a cell and/or a tissue. Specific examples of the body fluid include blood, extravascular tissue fluids (such as plasma, lymph, an edema fluid, an ascites fluid, a pleural fluid, and a cerebrospinal fluid), and digestive juices (such as a gastric juice, bile, a pancreatic juice, and saliva).

Figure 1:
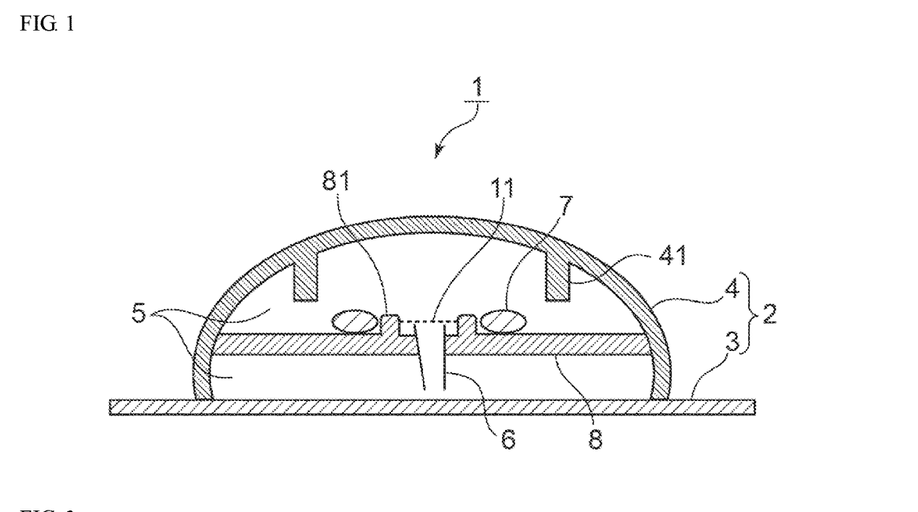
FIG. 1 is a schematic cross-sectional view for illustrating one state of a testing device according to one embodiment of the present invention.

FIG. 1 is a schematic cross-sectional view for illustrating a state of a testing device according to one embodiment of the present invention before an operation for collecting a body fluid. A testing device 1 includes a housing 2. The housing 2 includes a skin surface sheet 3 and an upper surface cover 4. Typically, the periphery of the skin surface sheet 3 is located on the outside of the outer periphery of the upper surface cover 4, and consequently, the housing 2 defines a closed space 5. A plurality of upper surface covers 4 may be arranged on the skin surface sheet 3 (not shown). In such configuration, the testing device 1 can be divided into a plurality of sections.

As a shape of the testing device 1 in plan view, any appropriate shape may be employed, and examples of the shape may include circular shapes and polygonal shapes (for example, tetragonal shapes, hexagonal shapes, and dodecagonal shapes).

The skin surface sheet 3 can adhere tightly to a skin 92 of a test subject 9. As the test subject 9, any appropriate test subject is given, and examples thereof include vertebrates (for example, humans). As the skin 92, any appropriate skin is given. The term "skin" as used herein refers to a concept including epithelium (for example, epidermis and mucosal epithelium), mesothelium, and endothelium. Examples of the epidermis include distal epidermis and topical epidermis. Examples of the mucosal epithelium include oral epithelium and gastrointestinal epithelium. Examples of the mesothelium include pleura and peritoneum. An example of the endothelium is vascular endothelium.

The upper surface cover 4 has elasticity. It should be noted that the phrase "a member has elasticity" as used herein refers to that the member as a whole has a property of deforming by application of an external force and recovering to an original shape by elimination of the external force. Accordingly, when the member as a whole has the above-mentioned property, the member has elasticity even if the member contains a component having no elasticity.

In the illustrated example, the upper surface cover 4 includes, on the inner surface of the housing 2, an upper spacer 41 that projects in the direction of the skin surface sheet 3. It should be noted that, in this description, the direction of the skin surface sheet is not required to be a completely vertical direction with respect to the skin surface sheet 3 and includes a direction within a range of preferably ±20°, more preferably ±10°, even more preferably ±5° with respect to the vertical direction. The same applies to the opposite direction to the skin surface sheet.

A hollow needle 6 and testing means (for example, testing reagent) 7 are accommodated inside the housing 2.

The hollow needle 6 interlocks with the upper surface cover 4. Specifically, when the upper surface cover is deformed by applying an external force in the direction of the skin surface sheet to the upper surface cover, the hollow needle can move toward the direction of the skin surface sheet.

In the illustrated example, the hollow needle 6 is supported by an inner support 8 arranged in the upper surface cover 4 on the inside of the housing 2. Typically, the hollow needle 6 is supported so that the tip of the needle is directed to the skin surface sheet 3.

The testing means 7 is accommodated inside the housing 2, and hence the test subject 9 can avoid a direct look at a body fluid collecting operation. In the illustrated example, the testing means 7 is arranged on the surface of the inner support 8 on the side opposite to the skin surface sheet 3.

In the illustrated example, the inner support 8 has a sheet shape and is supported by the upper surface cover 4 so that the inner support 8 is approximately parallel to the skin surface sheet 3. The hollow needle 6 supported by the inner support 8 penetrates the inner support 8. The inner support 8 may have elasticity. In such configuration, the interlocking property of the hollow needle 6 with the upper surface cover 4 is more stabilized. It should be noted that the term "approximately parallel" as used herein refers to an angle that is different from an exactly parallel angle by preferably ±20°, more preferably ±10°, even more preferably ±5°.

In the illustrated example, the inner support 8 includes a lower spacer 81 configured to project in the opposite direction to the skin surface sheet 3. The lower spacer 81 is arranged so as to surround the hollow needle 6. The lower spacer 81 is arranged inside the testing means 7. The lower spacer 81 may have, for example, a columnar shape (for example, hollow cylindrical shape and hollow prismatic shape). The lower spacer 81 has a length equal to or longer than that of a projecting portion of the hollow needle 6 penetrating the inner support 8 on the side opposite to the skin surface sheet 3 (for example, 1.2 times or more, preferably 1.5 times or more as long as the length of the portion).

In the illustrated example, body fluid pretreatment means (for example, body fluid separation means such as filter paper) 11 is arranged inside the lower spacer 81 and on the hollow needle 6 on the side opposite to the skin surface sheet 3. The body fluid pretreatment means 11 may be arranged, for example, in the hollow needle 6, on the surface of the inner support 8 on the side opposite to the skin surface sheet 3, and at the same position as the testing means 7 (not shown).

Figure 2:
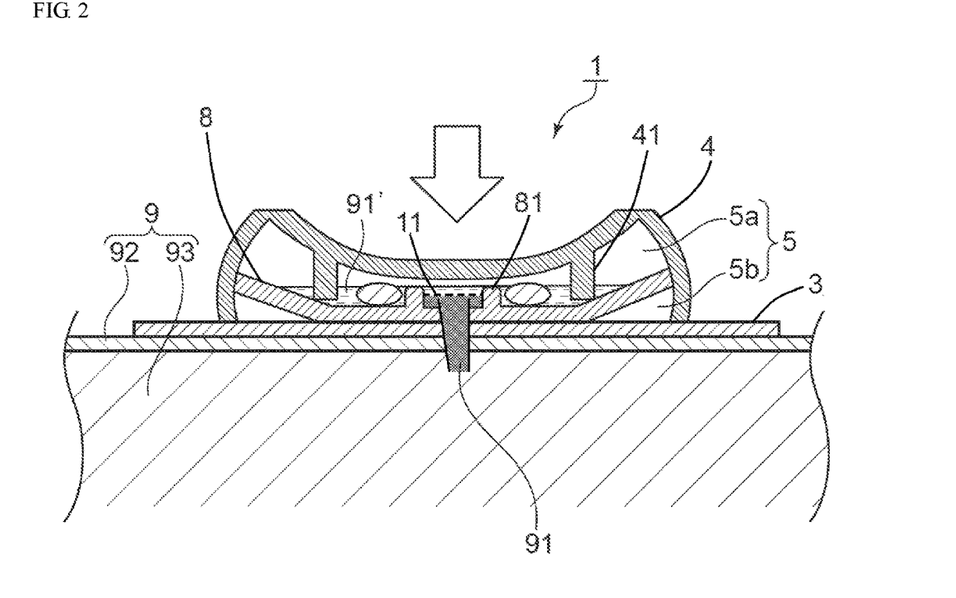
FIG. 2 is a schematic cross-sectional view for illustrating another state of the testing device according to one embodiment of the present invention.

FIG. 2 is a schematic cross-sectional view for illustrating the testing device 1 in a state in which the hollow needle penetrates the skin surface sheet to perforate the skin. When an external force in the direction of the skin surface sheet 3 is applied to the upper surface cover 4 with the skin surface sheet 3 adhering tightly to the skin 92 of the test subject 9 (for example, when the upper surface cover 4 is pressed), the upper surface cover 4 is deformed. As a result, as illustrated in FIG. 2, the inner support 8 is brought into contact with the skin surface sheet 3. The device is constructed so that the length of a projecting portion of the hollow needle 6 penetrating the inner support 8 on the skin surface sheet 3 side is longer than the total of the thickness of the skin surface sheet 3 and the thickness of the skin 92. Accordingly, the hollow needle 6 penetrates the skin surface sheet 3 to perforate the skin 92, and the tip of the hollow needle 6 reaches a tissue 93 including a body fluid 91. As the tissue 93, any appropriate tissue including a body fluid is given, and examples thereof include dermis, subcutaneous tissues, muscular tissues, and visceral tissues. The tip of the hollow needle 6 preferably reaches a tissue including a desired body fluid. When the body fluid 91 is blood, the tissue 93 may be a tissue (for example, dermis) having a blood vessel (for example, capillary blood vessel).

In the state illustrated in FIG. 2, the inner support 8 is brought into contact with the upper surface cover 4 via the upper spacer 41 (substantially, the inner support 8 is pressed via the upper spacer 41). In the state, the inner support 8 may be brought into contact with the upper surface cover 4 via the lower spacer 81 (the illustrated example is an illustration of a state in which the lower spacer 81 is not brought into contact with the upper surface cover 4). Further, the upper spacer 41 and/or the lower spacer 81 may have rigidity. In such configuration, excessive pushing of the hollow needle 6 in the test subject 9 can be prevented. It should be noted that the term "rigidity" as used herein refers to rigidity enough not to cause deformation by the above-mentioned external force.

In the illustrated example, the inner support 8 divides the space 5 inside the housing 2 into a space 5a communicating with the interior of the hollow needle 6 and a space 5b not communicating with the interior of the hollow needle 6 under the state in which the skin 92 is perforated. In such configuration, the volume of the space in which the body fluid is brought into contact with the testing means is limited, and hence information on the body fluid can be acquired more easily even when the amount of the body fluid 91 flowing therein is small. Further, the space 5a is defined on the side opposite to the skin surface sheet 3 with respect to the inner support 8. Accordingly, the body fluid having flowed therein is brought into contact with the testing means 7 on the side opposite to the skin surface sheet 3 with respect to the inner support 8, and hence information on the body fluid can be acquired easily.

The space 5a (substantially the space 5) can be maintained in a reduced pressure state until the hollow needle 6 perforates the skin 92. When the space is maintained in a reduced pressure state, the efficiency of collecting the body fluid can be improved.

In the state illustrated in FIG. 2, the body fluid 91 flows in the space 5a through the hollow needle 6. The body fluid flowing therein includes not only a body fluid flowing therein during application of the external force but also a body fluid flowing therein after elimination of the external force. As a mechanism of flowing of the body fluid 91 in the space 5a through the hollow needle 6, there are given, for example, flowing of the body fluid 91 therein based on a capillary action, flowing of the body fluid 91 therein by recovering the upper surface cover 4 to the original shape, and suction of the body fluid 91 by the space 5a in a reduced pressure state.

The body fluid having flowed therein may be or may not be subjected to pretreatment. In the illustrated example, the body fluid 91 having flowed therein is subjected to pretreatment by the body fluid pretreatment means 11, and a body fluid 91' having been subjected to the pretreatment is brought into contact with the testing means 7. The pretreatment for the body fluid can facilitate detection of an object to be measured, can remove impurities, and can deactivate infectious microorganisms, for example. Thus, the pretreatment can improve the quality of information acquired or can further reduce infection risks.

Figure 3:
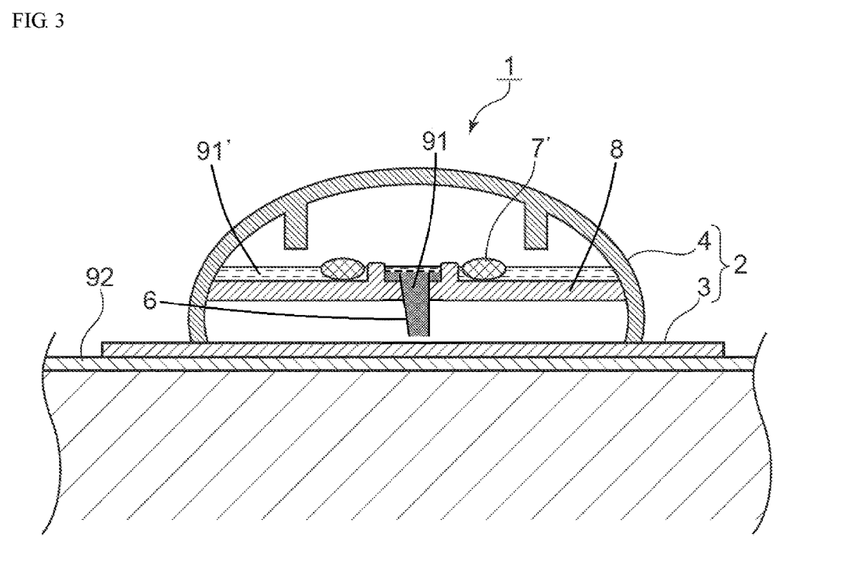
FIG. 3 is a schematic cross-sectional view for illustrating still another state of the testing device according to one embodiment of the present invention.

FIG. 3 is a schematic cross-sectional view for illustrating the testing device 1 in a state in which the upper surface cover has been recovered to the original shape by elimination of an external force. When the external force in the direction of the skin surface sheet 3 is eliminated, the upper surface cover 4 having elasticity is recovered to the original shape. As a result, the inner support 8 interlocks with the upper surface cover 4, and the hollow needle 6 supported by the inner support 8 becomes again accommodated in the housing 2. It should be noted that the term "original shape" as used herein may refer to an approximately original shape such that the inner support and the hollow needle supported by the inner support can become again accommodated as described above and does not necessarily refers to a completely original shape.

After the contact of the body fluid with the testing means, the testing means provides acquirable information on the body fluid. The term "acquirable" refers to, for example, information that can be acquired by a sense of a human, preferably information that can be visually recognized. When the information is provided as information that can be acquired by a sense of a human, the information can be acquired by a more simple operation. In addition, when the information is provided as information that can be visually recognized, results of the test can be judged at a place in which the body fluid is collected, and the information on the body fluid can be digitalized easily to ensure objectivity. As means for digitalizing the information, there are given, for example, photographing equipment (for example, a digital camera) and measurement equipment (for example, a turbidity measurement apparatus, a luminescence measurement apparatus, a fluorescence measurement apparatus, and a color measurement apparatus).

In the state illustrated in FIG. 3, after contact of the testing means 7 with the body fluid 91', the testing means 7 has changed into a state in which information on the body fluid can be visually recognized. The testing means 7 having changed as described above is denoted by reference sign 7' in the figure. Examples of the change include changes in shape, turbidity, luminescence, color tone, and fluorescence, and a combination of all or part of the changes. The change may occur in the testing means as in the illustrated example, in the body fluid, or in both of the body fluid and the testing means.

Figure 4:
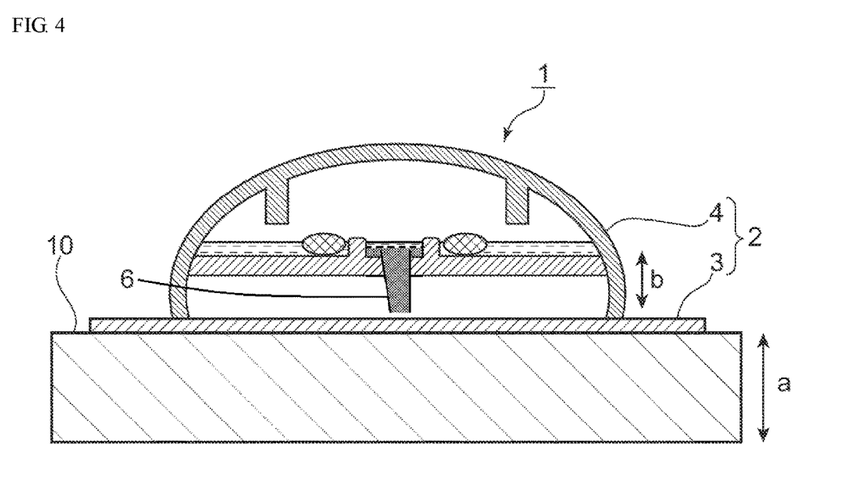
FIG. 4 is a schematic cross-sectional view for illustrating still another state of the testing device according to one embodiment of the present invention.

FIG. 4 is a schematic cross-sectional view for illustrating the testing device 1 in a state in which the testing device has been peeled off from the skin after collection of a body fluid. The testing device 1 may further include, as another member, a lower surface cover 10 attachable to the surface of the skin surface sheet 3 on the outside of the housing 2 (hereinafter sometimes referred to as surface of the skin surface sheet 3). As illustrated in FIG. 4, after peel-off of the testing device 1 after collection of the body fluid from the skin 92, the lower surface cover 10 may be attached to the surface of the skin surface sheet 3. The lower surface cover 10 has a thickness a equal to or longer than a length b of the whole of the hollow needle 6 (for example, 1.2 times or more, preferably 1.5 times or more as long as the length b). In such configuration, when the lower surface cover 10 is attached to the surface of the skin surface sheet 3 of the testing device 1 after collection of the body fluid, exposure of the tip of the hollow needle 6 to the outside can be prevented even when, for example, the hollow needle 6 penetrates the skin surface sheet 3 by accidentally applying an external force again to the upper surface cover 4. Accordingly, infection risks can further be reduced to improve safety in disposal, which may enable disposal of the device as a general waste.

The lower surface cover 10 is typically attached so as to cover a position that is on the surface of the skin surface sheet 3 and corresponds to the hollow needle 6. The lower surface cover 10 may be attached so that the periphery of the lower surface cover 10 is located on the outside of a portion corresponding to the outer periphery of the upper surface cover 4 on the surface of the skin surface sheet 3. In the illustrated example, the lower surface cover 10 is attached so that the periphery of the lower surface cover 10 is located on the outside of the outer periphery of the skin surface sheet 3. In such configuration, the portion corresponding to the outer periphery of the upper surface cover 4 on the surface of the skin surface sheet 3 is covered by the lower surface cover 10, and hence leakage of the body fluid to the outside of the testing device is less liable to occur, which can further reduce infection risks. The lower surface cover 10 may be formed of any appropriate material as long as exposure of the hollow needle 6 can be prevented appropriately.

Figure 5:
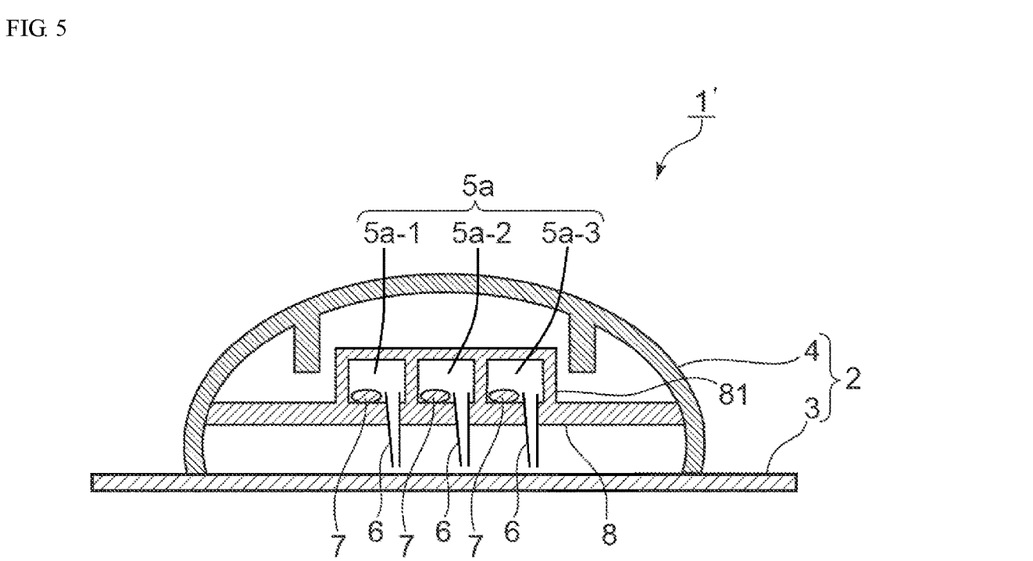
FIG. 5 is a schematic cross-sectional view of a testing device according to another embodiment of the present invention.

FIG. 5 is a schematic cross-sectional view of a testing device 1' according to another embodiment of the present invention. In the illustrated example, in the testing device 1', a plurality of hollow needles 6 are accommodated in the housing 2. In the illustrated example, a plurality of lower spacers 81 each having a columnar shape in which the end on the side opposite to the skin surface sheet 3 is closed are arranged. Further, the lower spacers 81 adjacent to each other are connected via the side surfaces of the spacers. Thus, the space 5a communicating with the interiors of the hollow needles 6 is divided into a plurality of spaces 5a-1, 5a-2, 5a-3, . . . , which do not communicate with each other. The hollow needles 6 are arranged in the respective spaces 5a-1, 5a-2, 5a-3, . . . . Testing means 7 are arranged in the respective spaces 5a-1, 5a-2, 5a-3, . . . . All of the testing means 7 arranged in the respective spaces may all be testing means for acquiring the same information or testing means for acquiring different information, or may include testing means for acquiring the same information and testing means for acquiring different information. In such configuration, a plurality of pieces of information on a body fluid can be acquired through one operation, which can improve accuracy of the test or can increase test items. More specifically, when a plurality of pieces of the same kind of information are acquired, for example, it is possible to eliminate an abnormal value or to calculate a mean value, with the result that accuracy of the test can be improved. In addition, when a plurality of different kinds of information are acquired simultaneously, for example, it is possible to simultaneously test a plurality of different kinds of particular components or to expand a measurable range by using a plurality of testing means having different measurable ranges, with the result that test items can be increased. Accordingly, the device is particularly effective for, for example, measurement of the amount of a particular component (for example, blood sugar level) in a body fluid and detection of a plurality of particular components (for example, various antigens such as blood group antigens and nucleic acids having various sequences).

Figure 6:
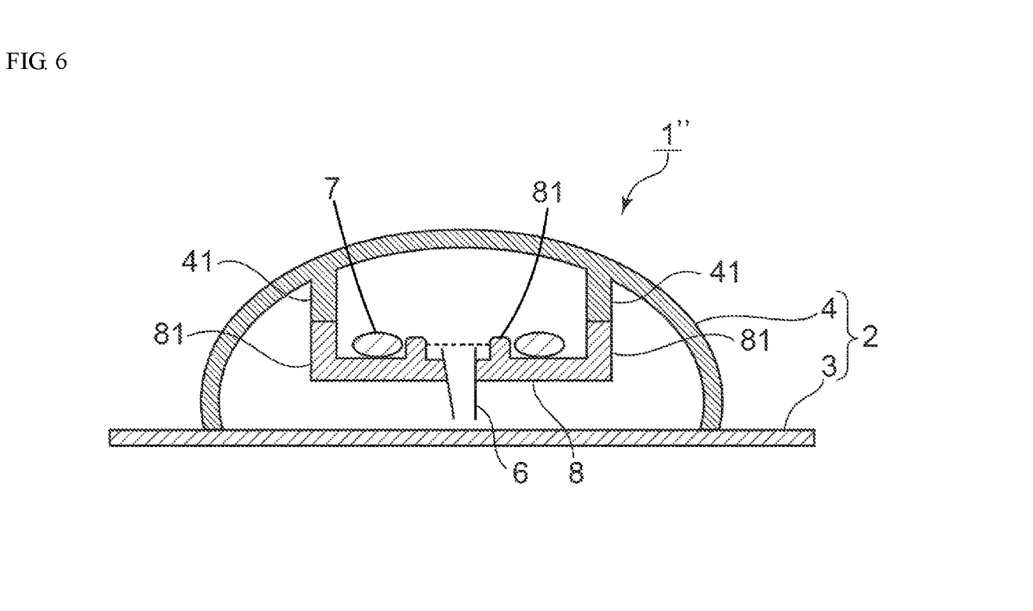
FIG. 6 is a schematic cross-sectional view of a testing device according to still another embodiment of the present invention.

FIG. 6 is a schematic cross-sectional view of a testing device 1" according to still another embodiment of the present invention. In the illustrated example, as a lower spacer 81 configured to project from the inner support 8 toward the opposite direction to the skin surface sheet 3, a lower spacer 81 is arranged on the outside of the testing means 7 in addition to the lower spacer 81 surrounding the hollow needle 6 and arranged on the inside of the testing means 7. The inner support 8 is supported by the upper surface cover 4 such that the inner support 8 is approximately parallel to the skin surface sheet 3 by connecting the lower spacer 81 arranged on the outside of the testing means 7 to the upper spacer 41 configured to project from the upper surface cover 4 toward the direction of the skin surface sheet 3. The upper spacer 41 and/or the lower spacer 81 may have rigidity. In addition, the inner support 8 (excluding the lower spacer 81) may have rigidity. In such configuration, a distance between the upper surface cover 4 and the inner support 8 can be secured by the upper spacer 41 and the lower spacer 81 while the hollow needle 6 perforates the skin 92, and hence excessive pushing of the hollow needle 6 in the test subject 9 can be prevented.

Figure 7:
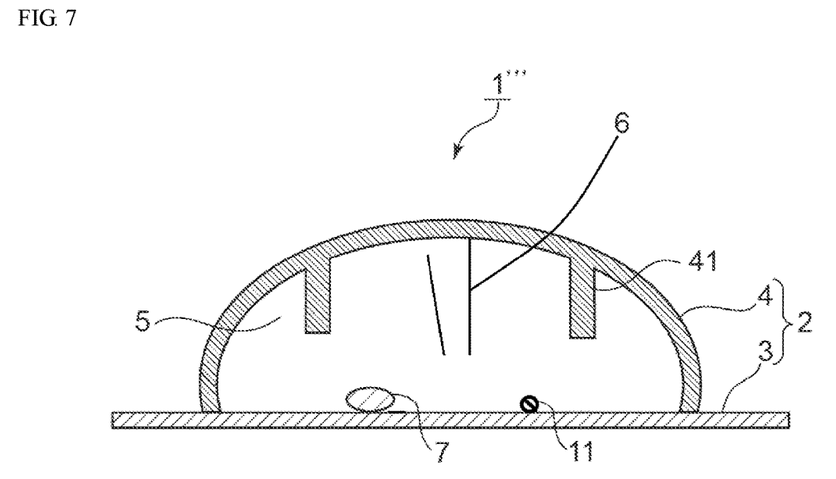
FIG. 7 is a schematic cross-sectional view for illustrating one state of a testing device according to still another embodiment of the present invention.

FIG. 7 is a schematic cross-sectional view for illustrating a testing device 1''' according to still another embodiment of the present invention in a state before an operation for collecting a body fluid. In the illustrated example, no inner support 8 is arranged in the testing device 1'''. The hollow needle 6 is supported directly by the upper surface cover 4 on the inside of the housing 2. The hollow needle 6 has an outlet on its side surface in the vicinity of the end of the needle on the side opposite to the skin surface sheet 3. The testing means 7 is arranged on the surface of the skin surface sheet 3 on the inside of the housing 2. The body fluid pretreatment means (for example, cell aggregation prevention means, such as heparin) 11 is arranged on the surface of the skin surface sheet 3 on the inside of the housing 2.

Figure 8:
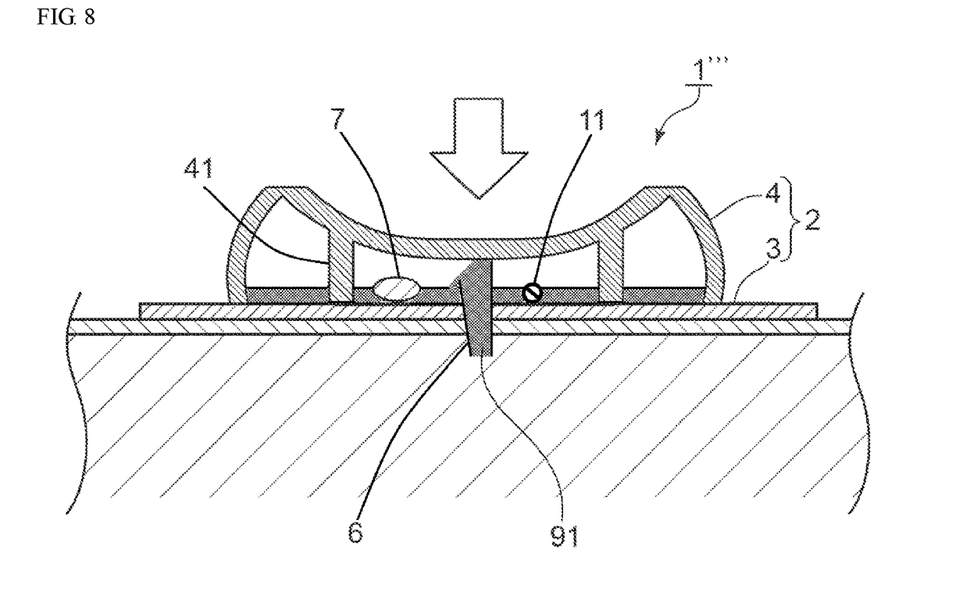
FIG. 8 is a schematic cross-sectional view for illustrating another state of the testing device according to still another embodiment of the present invention.

FIG. 8 is a schematic cross-sectional view for illustrating the testing device 1''' in a state in which the hollow needle penetrates the skin surface sheet to perforate the skin.

In the state illustrated in FIG. 8, the skin surface sheet 3 is brought into contact with the upper surface cover 4 via the upper spacer 41. In such configuration, excessive pushing of the hollow needle 6 in the test subject 9 can be prevented.

In the state illustrated in FIG. 8, the body fluid 91 flows in the skin surface sheet 3 on the inside of the housing 2 through the hollow needle 6. The body fluid 91 having flowed therein is brought into contact with the body fluid pretreatment means 11 and the testing means 7 to provide acquirable information on the body fluid.

The members of the testing device are additionally described below.

A-2. Skin Surface Sheet

At least part of the skin surface sheet (for example, a position corresponding to the hollow needle) may be formed of a material having elasticity (for example, rubber (such as butyl rubber), latex, silicone, and a thermoplastic elastomer). In such configuration, a penetration site in the skin surface sheet can be closed easily after the hollow needle becomes again accommodated in the housing. Thus, leakage of the body fluid collected to the outside of the testing device is less liable to occur, which further improves safety of the testing device.

An adhesive may be applied to the surface of the skin surface sheet 3 (the surface of the skin surface sheet 3 on the outside of the housing 2) (not shown). In such configuration, the testing device can be fixed more firmly to the skin.

The adhesive may contain a pain reducing component. When the pain reducing component penetrates the skin, a pain sensation around the testing device can be reduced to ameliorate pain of the test subject. Further, the adhesive can prevent the test subject from going on a rampage owing to the pain, and hence safety of healthcare professionals can further be improved. It should be noted that, instead of addition of the pain reducing component to the adhesive, the testing device may further include, as another member, a pain reducing sheet, which can adhere tightly to the skin and has a pain reducing component on the surface to adhere tightly to the skin. In such configuration, the pain sensation of the test subject can be reduced by allowing the pain reducing sheet to adhere tightly to the skin in advance and allowing the skin surface sheet to adhere tightly to the skin from above the pain reducing sheet. It should be noted that the state in which the skin surface sheet adheres tightly to the skin includes not only a case where the skin surface sheet directly adheres tightly to the skin but also a case where the skin surface sheet adheres tightly to the skin surface via a sheet that is used as another member and can adhere tightly to the skin.

In both of the case where the adhesive in the skin surface sheet contains the pain reducing component and the case where the testing device includes the pain reducing sheet, specific examples of the pain reducing component include an anesthetic component and an analgesic component (for example, menthol and an appropriate Chinese herbal medicine component). Examples of the anesthetic component include an ester-type local anesthetic agent and an amide-type local anesthetic drug. Examples of the ester-type local anesthetic agent include cocaine, procaine, chloroprocaine, tetracaine, and ethyl aminobenzoate (benzocaine). Examples of the amide-type local anesthetic drug include lidocaine, mepivacaine, dibucaine, bupivacaine, ropivacaine, and levobupivacaine. In addition to the pain reducing component, a pain reducing component penetration assisting drug for assisting subcutaneous penetration of the pain reducing component may further be mixed.

A-3. Upper Surface Cover

At least part (for example, a position corresponding to the opposite direction to the skin surface sheet with respect to a position at which the testing means is arranged) of the upper surface cover may be formed of a material capable of transmitting visible light. Any appropriate material may be used as the material capable of transmitting visible light, and examples thereof include a polycarbonate resin, a polyester-based resin, an acrylic resin, a polyolefin resin, and glass. In such configuration, the interior of the housing can be observed easily from the upper surface cover side of the testing device, and hence information on the body fluid collected can be acquired more easily. The information can be acquired particularly easily while the testing device adheres tightly to the skin of the test subject.

At least part (for example, a portion excluding the portion formed of the material capable of transmitting visible light and the upper spacer) of the upper surface cover may be formed of a material having elasticity (for example, rubber (such as butyl rubber), latex, silicone, and a thermoplastic elastomer). In such configuration, the above-mentioned elasticity can be easily obtained.

A material for the upper spacer may be a metal material or a non-metal material, or a combination thereof.

Examples of the metal material include iron, aluminum, nickel, magnesium, titanium, and alloys containing the metals.

Examples of the non-metal material include synthetic or natural resin materials. Examples of the resin material include a polyester-based resin, a polyolefin-based resin, and hard rubber.

A-4. Hollow Needle

As a shape of the outside of the hollow needle, any appropriate shape is given, and examples thereof include an approximately conical shape (for example, approximately circular conical shape and approximately pyramidal shape), and an approximately columnar shape (for example, approximately cylindrical shape and approximately prismatic shape). The hollow needle may have a shape configured to taper toward the tip. The hollow part of the hollow needle can be specified according to the shape of the outside of the hollow needle.

The hollow needle may have any appropriate length enough to reach a tissue including a desired body fluid. Specifically, the length of the hollow needle is, for example, from 0.1 mm to 20 cm, preferably from 1 mm to 10 cm. In order to collect blood subcutaneously, for example, the length is preferably from about 0.5 mm to about 1 cm, and in order to collect a body fluid (for example, digestive juice) in an organ, for example, the length is preferably from about 6 cm to about 20 cm.

The length of a projecting portion of the hollow needle penetrating the skin surface sheet in perforation of the skin is, for example, from 5 µm to 20 cm, preferably 10 µm to 10 cm. For example, in order to collect blood subcutaneously, the length of the projecting portion is preferably from about 5 µm to about 1 mm, and for example, in order to collect a body fluid (for example, digestive juice) in an organ, the length is preferably from about 5 cm to about 15 cm.

The diameter of the hollow needle may be adjusted to one enough to collect a required amount of the body fluid by a collection operation depending on test items.

A material for the hollow needle may be a metal material or a non-metal material, or a combination thereof Examples of the metal material include iron-containing alloys (such as stainless steel).

The non-metal material may be a synthetic or natural resin material. Examples of the non-metal material include polylactic acid, polyglycolide, polylactic acid-co-polyglycolide, caprolactone, polyurethane, polyanhydride, a polysaccharide, polycarbonate, polymethacrylic acid, ethylene vinyl acetate, polytetrafluoroethylene, and polyoxymethylene.

The non-metal material may be a biodegradable polymer. Examples of the biodegradable polymer include polylactic acid, polyglycolide, polylactic acid-co-polyglycolide, caprolactone, polyurethane, polyanhydride, and a polysaccharide. Examples of the polysaccharide include hyaluronic acid, pullulan, dextran, dextrin, and chondroitin sulfuric acid. Of those, polylactic acid is preferred. In such configuration, safety of the testing device can further be improved.

A-5. Inner Support

As a material for the inner support (excluding the lower spacer part), there are given, for example, a material listed as the material having elasticity of the materials for the upper surface cover, and a material similar to the material for the upper spacer.

As a material for the lower spacer arranged at the inner support, for example, a material similar to the material for the upper spacer is given.

A-6. Testable Information

As the information on the body fluid, any appropriate information is given, and specific examples thereof may include information described in a variety of practice guidelines (for example, Medical Information Service Minds, National Guideline Clearinghouse, and National Institute for Health and Clinical Excellence). Further, there may be given, for example, the presence amount of a particular component in the body fluid, a chemical property (for example, pH) of the body fluid, a physical property (for example, viscosity) of the body fluid, and a biological property (for example, immunoactivity) of the body fluid. It should be noted that the term "presence amount of a particular component" as used herein refers to a concept including not only a quantitative presence amount but also a qualitative presence amount (for example, the presence or absence of the particular component and/or information on whether the amount of the particular component is large or small) and a semi-quantitative presence amount.

Examples of the particular component include an antibody against a particular substance, an antigen to be recognized by a particular antibody, a drug, a protein, an amino acid, a saccharide, a lipid, an electrolyte, a vitamin, a nucleic acid, and other physiologically active substances (such as a peptide, a cytokine, a chemokine, and a hormone), and metabolites thereof.

The particular component may be a substance derived from the test subject, or may be a substance derived from a microorganism.

Examples of the substance derived from a microorganism include any appropriate substances each of which may serve as an antigen of an antibody (such as a protein and a polysaccharide) and nucleic acids (such as DNA and RNA). It should be noted that the term "microorganism" as used herein refers to a concept including bacteria, filamentous fungi, and viruses. Specific examples of the microorganism include microorganisms having effects on health of the test subject (such as infectious microorganisms).

As the antibody against a particular substance, for example, an antibody against the substance derived from a microorganism (for example, an antibody derived from the test subject) is given. Specific examples of the antigen to be recognized by a particular antibody include an antigen on the surface of a cell (for example, an antigen for specifying a blood type (for example, AB group antigen and HLA antigen)). As the drug, for example, a drug administered to the test subject is given. Specific examples of the protein include a marker protein (for example, an infection marker (for example, CRP) and glycated hemoglobin) capable of reflecting health of the test subject, and an antibody. In addition to those particular components, amino acids, saccharides, lipids, electrolytes, vitamins, nucleic acids, and other physiologically active substances have effects on health of the test subject. Therefore, when the presence amounts of those substances and metabolites of the substances are measured, information that is very important in judgment of the health of the test subject can be acquired. Specific examples thereof may include blood sugar involved in diabetes, and an electrolyte (for example, potassium ion) in a patient with renal failure receiving dialysis treatment.

A-7. Testing Means

A-7-1. Outline of Testing Means

The testing means may have, for example, a form of a reagent (testing reagent), a form of equipment (testing equipment), or a form obtained by combining the reagent and the equipment.

The testing reagent may be in a liquid state or in a dried (solid) state, for example. The testing reagent may have, for example, a form by which the reagent is dissolved by contact with a body fluid having flowed therein.

The testing reagent may contain a marker molecule, for example. As the marker molecule, a substance causing an acquirable change (for example, visually detectable change) is given. As the acquirable change, there are given, for example, changes in shape, turbidity, luminescence, color tone, and fluorescence, and a combination of all or part of the changes.

As the marker molecule, for example, aggregation marker molecules (for example, latex particles and gold colloids) are given. When the aggregation marker molecules are used, an aggregation state of the aggregation marker molecules changes depending on information on the body fluid to provide a state in which the information on the body fluid is acquirable (for example, a state in which turbidity and/or color tone has changed).

As the marker molecule, there is given, for example, a substance capable of changing a state of color tone, luminescence, and/or fluorescence. The change in the state of color tone, luminescence, and/or fluorescence may be caused by a chemical reaction. As the chemical reaction, there is given, for example, an oxidation reaction and/or a reduction reaction.

The testing reagent may include an enzyme, for example. When a chemical reaction caused by an enzyme can be used, measurement can be carried out easily and sensitively. An example of the enzyme is glucose oxidase capable of reacting with glucose to provide reduction ability.

The testing equipment may include an electrode, for example. The electrode is particularly preferably used for measurement of the concentration of a particular sugar in the body fluid, the concentration of a particular electrolyte in the body fluid, and the oxidation-reduction potential of the body fluid, and/or the pH of the body fluid.

A-7-2. Particular Component Measurement Means

When the information on the body fluid is the presence amount of a particular component in the body fluid, the testing means preferably includes particular component measurement means. The term "particular component measurement means" as used herein refers to means for measuring the presence amount of a particular component. The particular component measurement means may be used in combination with another testing means.

The particular component measurement means may include a nucleic acid (for example, a nucleic acid containing a sequence complementary to a nucleic acid serving as the particular component in at least part thereof). The nucleic acid is preferably used when the particular component to be measured is a nucleic acid (for example, DNA and RNA). When the particular component measurement means includes a nucleic acid, measurement can be carried out easily and sensitively with improved specificity.

The particular component measurement means may include an antibody. The antibody is preferably used when the particular component to be measured is a substance that may be served as an antigen to be recognized by the antibody (for example, a protein and a polysaccharide). When the particular component to be measured is an antibody against a particular antigen, the particular component measurement means preferably includes a substance serving as an antigen against the antibody. In such case, measurement can be carried out easily and sensitively with high specificity.

A-7-3. Information Amplification Means

The testing means may include information amplification means for amplifying information on a body fluid. When the testing means includes the information amplification means, information can be acquired with further improved sensitivity.

As the information amplification means, for example, nucleic acid amplification means is given. The nucleic acid amplification means may typically include a nucleic acid. A specific example of the nucleic acid amplification means is a reagent to be used for an isothermal nucleic acid amplification method (for example, LAMP method). In such configuration, it is not necessary to change the temperature, and hence measurement can be carried out easily.

As the information amplification means, for example, an antibody (for example, an antibody capable of recognizing the particular component measurement means (for example, nucleic acid, antibody, and antigen)) may be given.

A-7-4. Specific Combination

The above-mentioned testing means may be used in combination. As a specific combination, there are given, for example, testing means including a product obtained by bonding a reagent included in the particular component measurement means and/or the information amplification means (for example, nucleic acid, antibody, and antigen) to the above-mentioned marker molecule (for example, aggregation marker molecule), testing means including a product obtained by bonding a reagent included in the particular component measurement means and/or the information amplification means (for example, nucleic acid, antibody, and antigen) to the above-mentioned enzyme, and testing means including a combination of the above-mentioned enzyme and the above-mentioned marker molecule (for example, a substance capable of changing a color tone, luminescence, and/or fluorescence state by a chemical reaction of the enzyme).

A-8. Body Fluid Pretreatment Means

As the body fluid pretreatment means, any appropriate means may be used. In addition, a plurality of body fluid pretreatment means may be used in combination.

Specific examples of the pretreatment performed by the body fluid pretreatment means include physical treatment (for example, separation such as filtration) and chemical treatment (for example, treatment with a drug and/or an enzyme). When the body fluid is blood, blood subjected to the pretreatment may be whole blood, blood from which blood cell components have been separated (for example, serum), or blood in which blood cell components have been destroyed.

The body fluid pretreatment means may have a form of a reagent, for example. When the body fluid pretreatment means has a form of a reagent, the body fluid pretreatment means may be present in a form of a reagent mixed with a testing reagent serving as the testing means. Further, the body fluid pretreatment means may be a dried reagent. The reagent may be one capable of being dissolved by contact with a body fluid having flowed therein.

Specific examples of the body fluid pretreatment means include body fluid separation means, cell aggregation prevention means, and body fluid component denaturation means.

As the body fluid separation means, any appropriate means for separating components in a body fluid depending on their properties is given. As the body fluid separation means, there is given, for example, means for separating components in a body fluid depending on their sizes, and a specific example thereof may be filtration means (for example, filter paper). The body fluid separation means may separate a body fluid into, for example, cell components and liquid components.

As the cell aggregation prevention means, there is given any appropriate means for preventing aggregation of at least part of cells in a body fluid, and specific examples thereof include heparin and sodium citrate. When aggregation of cells (for example, erythrocytes and platelets) in a body fluid is prevented, information on the body fluid collected can be acquired more easily.

As the body fluid component denaturation means, there is given any appropriate means for denaturing at least part of components in a body fluid. As the body fluid component denaturation means, there are given, for example, a surfactant (for example, an ampholytic surfactant and an anionic surfactant) and an enzyme (for example, a protease and a nuclease). As an object to be denatured by the body fluid component denaturation means, there are given, for example, a membrane component of cells in the body fluid (for example, cell membrane), a particular component to be measured, impurities inhibiting measurement, and microorganisms (for example, infectious microorganisms). When the object to be denatured is selected depending on situation, information on the body fluid collected can be acquired more easily, or infection risks can further be reduced.

A-9. Lower Surface Cover

An adhesive may be applied to the surface of the lower surface cover on the side attachable to the surface of the skin surface sheet. The adhesive can fix the lower surface cover firmly to the testing device.

At least part (for example, a position corresponding to the hollow needle in the lower surface cover attached to the surface of the skin surface sheet) of the lower surface cover may be formed of a material having elasticity (for example, rubber (such as butyl rubber), latex, silicone, and a thermoplastic elastomer). In such configuration, even when the tip of the hollow needle accidentally reaches the lower surface cover after attachment of the lower surface cover to the surface of the skin surface sheet, a spot formed on the lower surface cover can be closed easily. Accordingly, leakage of the body fluid collected to the outside of the testing device is less liable to occur, which further improves safety of the testing device.

B. Body Fluid Test Method

B-1. Outline of Body Fluid Test Method

A body fluid test method using the testing device of the present invention is described below.

The body fluid test method includes: a testing device tight adhesion step of allowing the skin surface sheet of the testing device to adhere tightly to the skin; a perforation step of perforating the skin by allowing the hollow needle to penetrate the skin surface sheet through deformation of the upper surface cover by application of an external force in the skin surface sheet direction to the upper surface cover after the testing device tight adhesion step; an information acquiring step of acquiring information on the body fluid after the perforation step; and a re-accommodating step of accommodating the hollow needle again within the inside of the housing by recovering the upper surface cover to the original shape by elimination of the external force after the perforation step.

The body fluid test method may substantially further include a peel-off step of peeling off the testing device from the skin after the re-accommodating step.

The body fluid test method may preferably further include a lower surface cover attaching step of attaching the lower surface cover to the surface of the skin surface sheet of the testing device after the peel-off step.

B-2. Testing Device Tight Adhesion Step

As a method of allowing the skin surface sheet of the testing device to adhere tightly to the skin, any appropriate method is given. Typically, as described in Section A-2 above, the surface of the skin surface sheet to which the adhesive has been applied is allowed to adhere tightly to the skin.

B-3. Perforation Step

As a method of applying the external force, there is given, for example, a method including pushing the upper surface cover. Examples of the means for applying the external force include fingers of a test subject and fingers of healthcare professionals.

The application of the external force may be started immediately after the skin surface sheet adheres tightly to the skin, or, for example, after the pain reducing component exhibits an effect.

B-4. Information Acquiring Step

As described above, when the testing device of the present invention is used, information on the body fluid can be acquired at the same place as a place where the body fluid has been collected without the need for a special operation for acquiring the information. Accordingly, misidentification of body fluid samples can be prevented.

The information acquiring step may be carried out independently of other steps (for example, the re-accommodating step, the peel-off step, and the lower surface cover attaching step). This is because the time between contact of the body fluid with the testing means and completion of acquisition of the information varies depending on the testing means.

Specifically, the information acquiring step may be carried out before or after the re-accommodating step, before or after the peel-off step, or before or after the lower surface cover attaching step.

B-5. Re-Accommodating Step

As a method of eliminating the external force, for example, stopping of the push in the direction of the skin surface sheet is given. The timing of start of elimination of the external force may be, for example, one immediately after confirming flowing of the body fluid in the space communicating with the interior of the hollow needle, contact of the body fluid having flowed therein with the testing means, and/or formation of a state in which the information on the body fluid can be acquired.

B-6. Peel-Off Step

The peel-off step is carried out after the re-accommodating step. More specifically, as the timing of start of the peeling, there may be given, for example, one after the hollow needle again becomes accommodated in the housing or one after the upper surface cover has recovered to the original shape. When the peel-off step is carried out at such timing, infection risks of healthcare professionals can be eliminated more certainly.

B-7. Lower Surface Cover Attaching Step

The lower surface cover attaching step is carried out after the peel-off step. More specifically, as the timing of the attachment, for example, there is given one immediately after peeling of the testing device. When the attachment is carried out at such timing, infection risks of healthcare professionals can be eliminated more certainly.

C. Body Fluid Collection Device

As a body fluid collection device of the present invention, there is given any appropriate body fluid collection device having the characteristics described in Section A above. Specifically, the body fluid collection device of the present invention may have a form obtained by omitting a test function from the above-mentioned testing device. Accordingly, the body fluid collection device of the present invention may take all embodiments described for the testing device except that the device is not required to acquire information on the body fluid collected, the testing means is not required to be accommodated in the housing, and the body fluid having flowed therein is not required to be brought into contact with the testing means.

D. Body Fluid Collection Method

As a method of collecting a body fluid using the body fluid collection device of the present invention, any appropriate body fluid collection method having the characteristics described in Section B above is given. Specifically, the body fluid collection method may have a form obtained by omitting the information acquiring step from the above-mentioned body fluid test method.

INDUSTRIAL APPLICABILITY

The body fluid collection device and the testing device of the present invention can be particularly suitably used in applications for testing a human's health condition.

REFERENCE SIGNS LIST 1 testing device
2 housing
3 skin surface sheet
4 upper surface cover
41 upper spacer
5 space inside housing
6 hollow needle
7 testing means
8 inner support
81 lower spacer
9 test subject
91 body fluid
92 skin
93 tissue
10 lower surface cover
11 body fluid pretreatment means

What is claimed is:

1. A body fluid collection device, comprising:
a housing including a skin surface sheet capable of adhering tightly to a skin and an upper surface cover, having elasticity, the upper surface cover being formed of a material capable of transmitting visible light; and
a hollow needle configured to interlock with the upper surface cover and accommodated in the housing,
wherein at least part of a space in the housing communicates with an interior of the hollow needle, and
wherein the body fluid collection device is configured such that:
through deformation of the upper surface cover by application of an external force in a direction of the skin surface sheet to the upper surface cover with the skin surface sheet adhering tightly to the skin, the hollow needle penetrates the skin surface sheet to perforate the skin, and a body fluid flows in the space communicating with the interior of the hollow needle through the hollow needle; and
through recovery of the upper surface cover to an original shape by elimination of the external force, the hollow needle again becomes accommodated in the housing,
wherein the body fluid collection device further comprises an inner support configured to support the hollow needle and arranged in the upper surface cover on an inside of the housing, and
wherein the inner support includes a lower spacer configured to project in an opposite direction to the skin surface sheet, and the lower spacer has a length equal to or longer than a length of a projecting portion of the hollow needle penetrating the inner support.

2. A testing device for collecting a body fluid and acquiring information on the body fluid collected, comprising:
a housing including a skin surface sheet capable of adhering tightly to a skin and an upper surface cover having elasticity, the upper surface cover being formed of a material capable of transmitting visible light;
a hollow needle configured to interlock with the upper surface cover and accommodated in the housing; and
testing means accommodated in the housing,
wherein at least part of a space in the housing communicates with an interior of the hollow needle, and
wherein the testing device is configured such that:
through deformation of the upper surface cover by application of an external force in a direction of the skin surface sheet to the upper surface cover with the skin surface sheet adhering tightly to the skin, the hollow needle penetrates the skin surface sheet to perforate the skin, and a body fluid flows in the space communicating with the interior of the hollow needle through the hollow needle and is brought into contact with the testing means to acquire information on the body fluid; and
through recovery of the upper surface cover to an original shape by elimination of the external force, the hollow needle again becomes accommodated in the housing,
wherein the testing device further comprises an inner support configured to support the hollow needle and arranged in the upper surface cover on an inside of the housing, and
wherein the inner support includes a lower spacer configured to project in an opposite direction to the skin surface sheet, and the lower spacer is arranged inside the testing means.

3. The testing device according to claim 2, wherein the inner support has a sheet shape and is supported by the upper surface cover so that the inner support is approximately parallel to the skin surface sheet.

4. The testing device according to claim 2,
wherein the hollow needle supported by the inner support penetrates the inner support, and
wherein the inner support divides the space in the housing into a space communicating with the interior of the hollow needle and a space not communicating with the interior of the hollow needle.

5. The testing device according to claim 2, wherein the inner support is brought into contact with the skin surface sheet when the hollow needle perforates the skin.

6. The testing device according to claim 2, wherein the upper surface cover includes, on an inner surface of the housing, an upper spacer configured to project in a direction of the skin surface sheet.

7. The testing device according to claim 2, wherein the space communicating with the interior of the hollow needle is maintained in a reduced pressure state until the hollow needle perforates the skin.

8. The testing device according to claim 2, further comprising, as another member, a lower surface cover attachable to a surface of the skin surface sheet, the lower surface cover having a thickness equal to or longer than a length of the hollow needle.

9. The testing device according to claim 2, further comprising body fluid pretreatment means arranged in the hollow needle and/or the space communicating with the interior of the hollow needle,
wherein the body fluid having flowed therein is subjected to pretreatment by the body fluid pretreatment means.

* * * * *